United States Patent
Brenner et al.

(10) Patent No.: US 9,493,740 B2
(45) Date of Patent: Nov. 15, 2016

(54) IMMUNOTHERAPY OF CANCER USING GENETICALLY ENGINEERED GD2-SPECIFIC T CELLS

(75) Inventors: Malcolm Brenner, Houston, TX (US); Gianpietro Dotti, Houston, TX (US); Nabil Ahmed, Houston, TX (US); Claudia Rossig, Heidelberg (DE); Stephen M. G. Gottschalk, Houston, TX (US); Zakaria Grada, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 518 days.

(21) Appl. No.: 13/820,931

(22) PCT Filed: Sep. 8, 2011

(86) PCT No.: PCT/US2011/050780
§ 371 (c)(1),
(2), (4) Date: Apr. 3, 2013

(87) PCT Pub. No.: WO2012/033885
PCT Pub. Date: Mar. 15, 2012

(65) Prior Publication Data
US 2014/0004132 A1 Jan. 2, 2014

Related U.S. Application Data

(60) Provisional application No. 61/380,761, filed on Sep. 8, 2010.

(51) Int. Cl.
| | |
|---|---|
| *C12N 5/00* | (2006.01) |
| *A61K 39/395* | (2006.01) |
| *C07K 16/28* | (2006.01) |
| *C12N 5/0783* | (2010.01) |
| *A61K 39/00* | (2006.01) |
| *C07K 16/18* | (2006.01) |

(52) U.S. Cl.
CPC ......... *C12N 5/0638* (2013.01); *A61K 39/0011* (2013.01); *C07K 16/18* (2013.01); *A61K 2039/5156* (2013.01); *A61K 2039/5158* (2013.01)

(58) Field of Classification Search
None
See application file for complete search history.

(56) References Cited

U.S. PATENT DOCUMENTS 6,509,016 B1   1/2003  Chatterjee et al.
2002/0102264 A1* 8/2002  Cheung ............... 424/155.1
2003/0148982 A1  8/2003  Brenner et al.
2007/0071759 A1* 3/2007  Shin et al. ............ 424/155.1
2010/0105136 A1  4/2010  Carter et al.

OTHER PUBLICATIONS

Sadelain et al. (Current Opinion in Immunology 2009, 21:215-223).*
Lo et al. (Cancer Res. 2010; 16(10): 2769-2780).*
Navid et al. (Curr Cancer Drug Targets. 2010; 10(2): 200-209).*
Furukawa et al., Ann. N.Y. Acad. Sci. 1086: 185-198 (2006).*
Pule et al., Molecular Therapy vol. 12: 933-941 (2005).*
Rossig et al., Blood. 2002; 99: 2009-2016.*
Wilkie et al., J Immunol 2008; 180: 4901-4909.*
Extended European Search Report issued in European Patent Application No. 11824106.6, dated Apr. 30, 2014.
Rossig et al., "Targeting of GD2-Positive Tumor Cells by Human T Lymphocytes Engineered to Express Chimeric T-Cell Receptor Genes", Int. J. Cancer, 94:228-236, 2001.
Won et al., "Immunotherapy of Metastatic Melanoma Using Genetically Engineered GD3-Specific T cells", Clinical Cancer Research, 15(18):5852-5860, 2009.
Pule et al., "Virus-specific T cells engineerd to coexpress turmor-specific receptors: persistence and antitumor activity in individuals iwnt neuroblastoma", Nature Medicine, 14(11):1264-1270, 2008.
Louis et al., "Treatment of High-Risk Neuroblastoma with Adoptively Transferred T Lymphocytes Genetically Engineered to Recognize GD2", Biology of Blood and Marrow Transplantation, 15(2):26, 2009.
Yoshida et al., "Ganglioside G(D2) in Small Cell Lung Cancer Cell Lines: Enhancement of Cell Proliferation and Mediation of Apoptosis", Cancer Research, May 15, 2001, pp. 4244-4252.
Zhao et al.,"GS2 Oligosaccharide: Target for Cytotoxic T Lymphocytes" The Journal of Experimental Medicine, Rockefeller University Press, US, vol. 182, Jul. 1, 1995, pp. 67-74.
Cheresh et al., "Biosynthesis and Expression of the Disialoganglioside GD2, a Relevant Target Antigen on Small Cell Lung Carcinoma for Monoclonal Antibody-mediated Cytolysis1", Cancer Research, vol. 46, Oct. 1, 1986, pp. 5112-5118.
Mujoo, et al., "Functional Properties and Effect on Growth Suppression of Human Neuroblastoma Tumors by Isotype Switch Variants of Monoclonal Antiganglioside GD2". American Association for Cancer Research, 2857-2861, 1989.
Imai, et al., "Complement-Mediated Mechanisms in Anti-GD2 Monoclonal Antibody Therapy for Murine Metastatic Cancer". American Association for Cancer Research, 10562-10568, 2005.
Agrawal V., et al.,14G2a anti-GD2 crossreactivity with the CD166 antigen., J Immunother.,1014-1015, Nov.-Dec. 2010;33(9).

* cited by examiner

*Primary Examiner* — Ilia Ouspenski
(74) *Attorney, Agent, or Firm* — Norton Rose Fulbright US LLP

(57) ABSTRACT

The present invention concerns immunotherapy for cancers having cells that comprise the ganglioside GD2 antigen. In specific embodiment, T cells having a chimeric receptor that targets GD2 is employed. In particular cases, the chimeric receptor comprises antibody, cytoplasmic signaling domain from the T cell receptor, and/or costimulatory molecule(s).

5 Claims, 13 Drawing Sheets

US 9,493,740 B2

IMMUNOTHERAPY OF CANCER USING GENETICALLY ENGINEERED GD2-SPECIFIC T CELLS

This application claims priority to U.S. Provisional Patent Application Ser. No. 61/380,761, filed Sep. 8, 2010, which is incorporated by reference herein in its entirety.

STATEMENT REGARDING FEDERALLY SPONSORED RESEARCH OR DEVELOPMENT

This invention was made with government support under PO1 CA94237 awarded by the National Institutes of Health. The government has certain rights in the invention.

TECHNICAL FIELD

The present invention generally concerns the fields of cell biology, molecular biology, and medicine. In particular, the field of the invention concerns immunotherapy of cancer.

BACKGROUND OF THE INVENTION

The rising incidence of cutaneous melanoma and the failure to significantly improve outcomes in metastatic disease have led to increasing interest in immunotherapeutic approaches, because these can be remarkably effective (Jemal et al., 2008; Bajetta et al., 2002; Rosenberg et al., 2008). Several investigators have focused on targeting tumor-associated antigens that fall into the cancer testis antigen group, including MAGE, BAGE, GAGE, and NY-ESO-1, or the melanocyte differentiation protein group, including gp100, Melan-A/MART-1, and tyrosinase, which are widely present on melanoma cells. These studies have used cytotoxic T cell lines (Mackensen et al., 2006; Butler et al., 2007), clones with native (Rosenberg et al., 2004) or transgenic αβ T cell receptors (Morgan et al., 2006) specific for cancer testis antigen-derived peptides that are recognized in association with human leukocyte antigen (HLA) class I antigens on the tumor cell surface. It is clear, however, that the heterogeneity of protein antigen expression and presentation in melanoma is a characteristic that helps limit the proportion of patients who are able to respond to such targeted strategies (Ohnmacht and Marincola, 2000). One means of increasing the effectiveness of targeted T cell therapy of melanoma, therefore, may be to use artificial chimeric receptors derived, for example, from the antigen binding domain of a monoclonal antibody (Pule et al., 2003). When coupled to appropriate intracellular signaling domains, T cells expressing these chimeric antigen receptors (CAR) can kill tumor cell targets (Haynes et al., 2002). They have the advantage of acting in a MHC unrestricted manner, allowing them to target tumor cells in which antigen processing or presentation pathways are disrupted. Moreover, they can be directed to nonpeptide antigens on the cell surface, broadening the range of target structures that can be recognized on malignant cells. Hence, CAR-expressing T cells could complement MHC restricted cytotoxic T cells, and increase the overall effectiveness of this cellular immunotherapy.

Many melanoma cells express a range of gangliosides, including GD2, GM2, GM3, and GD3, that may be a good choice of target for CAR-T cells, because their expression is highly tissue-restricted (Yun et al., 2000; Livingston, 1998). Although these carbohydrate antigens are expressed by both normal melanocytes and melanoma cells, expression is significantly up-regulated after malignant transformation of melanocytes (Tsuchida et al., 1989; Albino et al., 1992), and is associated with changes in the proliferation, migration, and metastatic potential of the tumor cells (Ravindranath et al., 2008). Moreover, natural or vaccine-induced antibodies to gangliosides in melanoma patients have been correlated with improved disease relapse-free survival (Livingston et al., 2008; Ragupathi et al., 2003).

BRIEF SUMMARY OF THE INVENTION

The present invention concerns methods and compositions for the treatment of cancer, including treatment of cancer employing immunotherapy. In particular cases, the immunotherapy includes T lymphocytes engineered to target certain cancers. Although any cancers may be targeted using the inventive therapy (including brain, breast, pancreatic, liver, kidney, lung, spleen, gall bladder, anal, testicular, ovarian, cervical, skin, bone, blood, or colon, for example), in particular cases the cancer is melanoma or lung cancer, including non small cell lung cancer. In specific embodiments, the cancer being treated has cancer cells with GD2 as an antigen on the surface of the cancer cells. In particular cases, the cytotoxic T lymphocytes (CTLs) employed to target GD2 on the surface of cancer cells comprise a receptor for GD2 and, in specific cases, the receptor on the CTLs is chimeric, non-natural and engineered at least in part by the hand of man. In particular cases, the engineered chimeric antigen receptor (CAR) has one, two, three, four, or more components, and in some embodiments the one or more components facilitate targeting or binding of the T lymphocyte to the GD2 antigen-comprising cancer cell, although in some cases one or more components are useful to promote T cell growth and maturity.

In certain embodiments, the present invention includes T lymphocytes engineered to comprise a chimeric receptor having an antibody for GD2, part or all of a cytoplasmic signaling domain, and/or part or all of one or more costimulatory molecules, for example endodomains of costimulatory molecules. In specific embodiments, the antibody for GD2 is a single-chain variable fragment (scFv), although in certain aspects the antibody is directed at other target antigens on the cell surface, such as HER2 or CD19, for example. In certain embodiments, a cytoplasmic signaling domain, such as those derived from the T cell receptor ζ-chain, is employed as at least part of the chimeric receptor in order to produce stimulatory signals for T lymphocyte proliferation and effector function following engagement of the chimeric receptor with the target antigen. Examples would include, but are not limited to, endodomains from co-stimulatory molecules such as CD28, 4-1BB, and OX40 or the signalling components of cytokine receptors such as IL7 and IL15. In particular embodiments, costimulatory molecules are employed to enhance the activation, proliferation, and cytotoxicity of T cells produced by the CAR after antigen engagement. In specific embodiments, the costimulatory molecules are CD28, OX40, and 4-1BB and cytokine and the cytokine receptors are IL7 and IL15.

Genetic engineering of human T lymphocytes to express tumor-directed chimeric antigen receptors (CAR) can produce antitumor effector cells that bypass tumor immune escape mechanisms that are due to abnormalities in protein-antigen processing and presentation. Moreover, these transgenic receptors can be directed to tumor-associated antigens that are not protein-derived, such as the ganglioside GD2, which is expressed in a high proportion of melanoma cells.

In certain embodiments, the present invention provides chimeric T cells specific for the ganglioside GD2 by joining an extracellular antigen-binding domain derived from the GD2-specific antibody sc14.G2a to cytoplasmic signaling domains derived from the T-cell receptor ζ-chain, with the endodomains of the exemplary costimulatory molecules CD28 and OX40, for examples. This CAR was expressed in human T cells and the targeting of GD2-positive melanoma tumors was assessed in vitro and in a murine xenograft, for example.

As described herein, upon coincubation with GD2-expressing melanoma cells, CAR-GD2 T lymphocytes incorporating the CD28 and OX40 endodomains secreted significant levels of cytokines in a pattern comparable with the cytokine response obtained by engagement of the native CD3 receptor. These CAR-T cells had antimelanoma activity in vitro and in an exemplary xenograft model, increasing the survival of tumor-bearing animals. Thus, redirecting human T lymphocytes to the tumor-associated ganglioside GD2 generates effector cells with antimelanoma activity that is useful in subjects with disease.

In some embodiments, there is a method of targeting a cancer cell having a GD2 antigen, comprising the steps of providing to the cell a cytotoxic T lymphocyte with a chimeric receptor that recognizes the GD2 antigen. In specific embodiments, the cancer cell is in vitro or in vivo. In certain embodiments, the chimeric receptor comprises antibody that binds GD2, such as a scFv antibody, for example the 14g2a scFv antibody.

In particular embodiments, the chimeric receptor comprises the effector domain of the T-cell receptor zeta chain or related signal transduction endodomains derived from the T cell receptor. In specific cases, the chimeric receptor comprises one or more costimulatory molecules, such as CD28, OX40, 4-1BB, or a combination thereof, for example. In specific embodiments, the cancer cell is in an individual with melanoma or non small cell lung cancer.

In one embodiment of the present invention, there is a method of treating melanoma or non small cell lung cancer in an individual, comprising the steps of administering to an individual cytotoxic T lymphocytes having a chimeric receptor that recognizes a GD2 antigen on the surface of cancer cells. In certain embodiments, the chimeric receptor comprises antibody that binds GD2, for example a scFv antibody, such as the 14g2a scFv antibody, as one instance.

In particular cases the chimeric receptor comprises the effector domain of the T-cell receptor zeta chain. In a specific embodiment, the chimeric receptor comprises one or more costimulatory molecules, such as CD28, OX40, 4-1BB, or a combination thereof, for example. In specific aspects, the individual has had and/or is having an additional cancer therapy for the respective melanoma or non small cell lung cancer.

The foregoing has outlined some of the features and technical advantages of the present invention in order that the detailed description of the invention that follows may be better understood. Additional features and advantages of the invention will be described hereinafter which form the subject of the claims of the invention.

BRIEF DESCRIPTION OF THE DRAWINGS

FIG. 2A shows expression of CAR-GD2 as assessed by FACS analysis using a specific 14.g2a anti-idiotype antibody (1A7). Graph is a representative expression of CAR-GD2 from four different transduced T cell lines. FIG. 2B shows that both CD4-positive and CD8-positive T lymphocytes expressed the CAR-GD2 after gene transfer.

In FIG. 5A, there are mean and SD of surviving cells expressing GFP for four T cell lines. In FIG. 5B, there is phenotypic analysis of coculture experiments.

FIG. 9A shows expression in small cell lung cancer. FIG. 9B shows expression in non-small cell lung cancer.

FIG. 12A shows killing of small cell lung cancer, and FIG. 12B shows killing of non-small cell lung cancer.

DETAILED DESCRIPTION OF THE INVENTION

Figure 1:
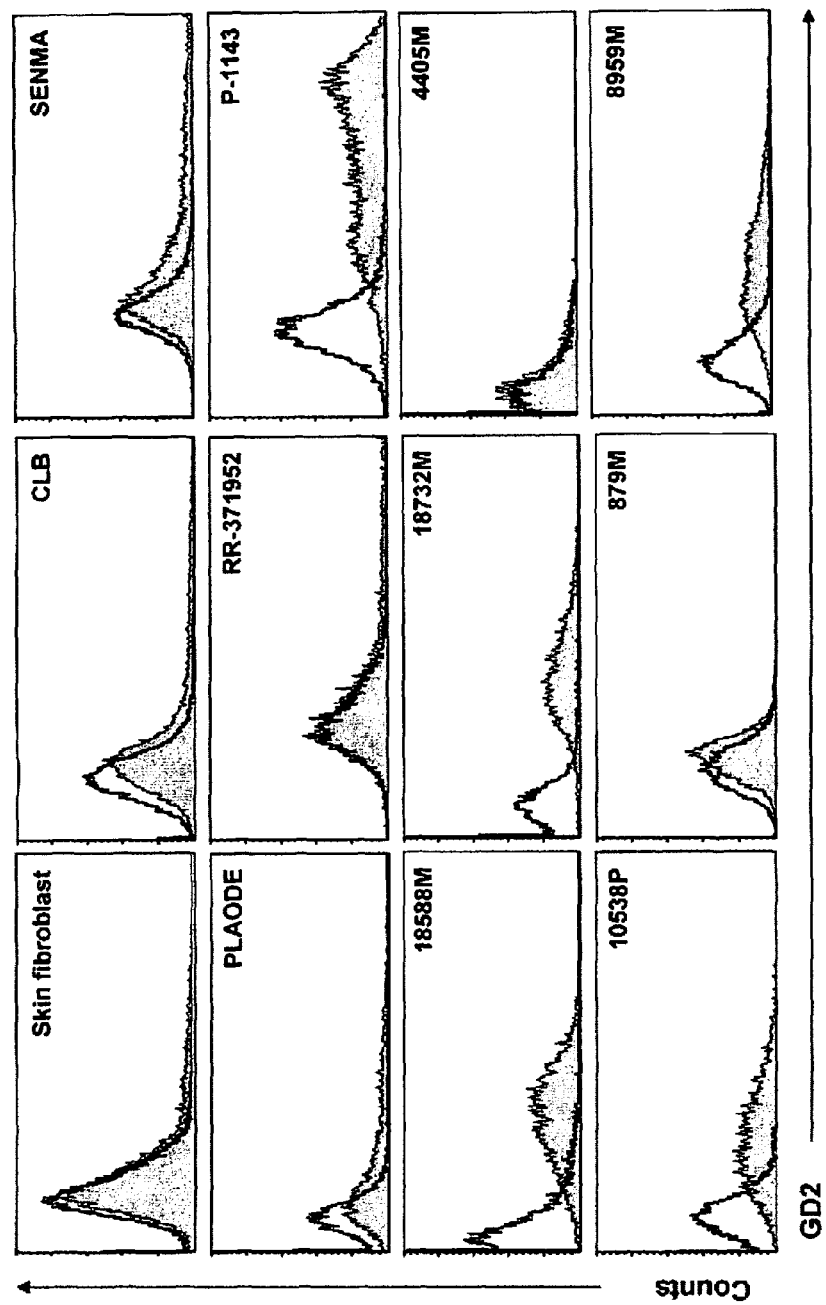
FIG. 1 shows expression of GD2 antigen in human melanoma cell lines. The expression of GD2 was evaluated by FACS analysis in 11 melanoma cell lines. Six (45%) and three (27%) tumor cell lines showed GD2 expression at intermediate/high (++/+++) or low levels (+), respectively. In two tumor cell lines (18%) GD2 was undetectable. A GD2-normal skin fibroblast line was used as a negative control for GD2 expression. Open histograms, isotype control of the GD2 staining (grey histograms).

In the following description, certain details are set forth such as specific quantities, sizes, etc. so as to provide a thorough understanding of the present embodiments disclosed herein. However, it will be obvious to those skilled in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

I. Definitions

As used herein, the term "costimulatory molecule" refers to a molecular component that promotes activation, proliferation and effector function of a T cell after engagement of an antigen specific receptor.

As used herein, the term "cytoplasmic signaling domain" refers to the component of a co-stimulatory molecule or cytokine receptor that exists inside the cell and is responsible for transducing the external signal received to the internal metabolic processes of the cell, thereby altering its phenotype and function.

In embodiments of the present invention, the overexpression of GD2 by human primary melanoma cells allows these cells to be targeted in vitro and in vivo by GD2 CAR-expressing primary T cells, and incorporation of endodomains from both CD28 and OX40 molecules (Pule et al., 2005) mediates costimulation of the T lymphocytes, inducing T cell activation, proliferation, and cytotoxicity against GD2-positive melanoma cells.

In particular embodiments of the invention, there are methods for killing metastatic melanoma cells using genetically manipulated T-cells that express a chimeric antigen receptor (CAR) directed against the ganglioside antigen GD2. Engagement (antigen binding) of this CAR leads to activation of the linked T-cell receptor ζ chain and the costimulatory molecules CD28 and OX40. The present invention leads to the suppression of metastatic melanoma xenografts in vivo, and the skilled artisan recognizes that such practices extrapolate to non small cell lung cancer, in certain embodiments.

II. scFv Antibodies

In particular embodiments of the invention, the CAR receptor comprises a single-chain variable fragment (scFv) that recognizes GD2. The skilled artisan recognizes that scFv is a fusion protein of the variable regions of the heavy (VH) and light chains (VL) of immunoglobulins, connected with a short linker peptide of ten to about 25 amino acids. The linker may be rich in glycine for flexibility and/or it may have serine or threonine for solubility, in certain cases. In a particular embodiment, the 14g2a scFv antibody is used in the CAR. The scFv may be generated by methods known in the art.

Other examples of ScFv made and successfully tested in pre-clinical studies include, but are not limited to, CD20, CD19, CD30, Her2, kappa light chain, and lambda light chain, and in certain embodiments one or more of these are employed in the invention.

In certain aspects, one can use cytokine exodomains or other ligand/receptor molecules as exodomains to provide targeting to the tumor cells.

III. Costimulatory Molecules

The skilled artisan recognizes that T cells utilize co-stimulatory signals that are antigen non-specific to become fully activated. In particular cases they are provided by the interaction between co-stimulatory molecules expressed on the membrane of APC and the T cell. In specific embodiments, the one or more costimulatory molecules in the chimeric receptor come from the B7/CD28 family, TNF superfamily, or the signaling lymphocyte activation molecule (SLAM) family. Exemplary costimulatory molecules include one or more of the following: B7-1/CD80; CD28; B7-2/CD86; CTLA-4; B7-H1/PD-L1; ICOS; B7-H2; PD-1; B7-H3; PD-L2; B7-H4; PDCD6; BTLA; 4-1BB/TNFRSF9/ CD137; CD40 Ligand/TNFSF5; 4-1BB Ligand/TNFSF9; GITR/TNFRSF18; BAFF/BLyS/TNFSF13B; GITR Ligand/ TNFSF18; BAFF R/TNFRSF13C; HVEM/TNFRSF14; CD27/TNFRSF7; LIGHT/TNFSF14; CD27 Ligand/ TNFSF7; OX40/TNFRSF4; CD30/TNFRSF8; OX40 Ligand/TNFSF4; CD30 Ligand/TNFSF8; TACI/ TNFRSF13B; CD40/TNFRSF5; 2B4/CD244/SLAMF4; CD84/SLAMF5; BLAME/SLAMF8; CD229/SLAMF3;

CD2 CRACC/SLAMF7; CD2F-10/SLAMF9; NTB-A/ SLAMF6; CD48/SLAMF2; SLAM/CD150; CD58/LFA-3; CD2; Ikaros; CD53; Integrin alpha 4/CD49d; CD82/Kai-1; Integrin alpha 4 beta 1; CD90/Thy1; Integrin alpha 4 beta 7/LPAM-1; CD96; LAG-3; CD160; LMIR1/CD300A; CRTAM; TCL1A; DAP12; TIM-1/KIM-1/HAVCR; Dectin-1/CLEC7A; TIM-4; DPPIV/CD26; TSLP; EphB6; TSLP R; and HLA-DR.

The CAR of the invention may employ one, two, three, four, or more costimulatory molecules.

IV. Effector Domain of the T-Cell Receptor Zeta Chain

The effector domain is a signalling domain that transduces the event of receptor ligand binding to an intracellular signal that partially activates the T lymphocyte. Absent appropriate co-stimulatory signals, this event is insufficient for useful T cell activation and proliferation.

V. Combination Therapy

In certain embodiments of the invention, methods of the present invention for clinical aspects are combined with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cancer cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir (Culver, et al., 1992). In the context of the present invention, it is contemplated that cell therapy could be used similarly in conjunction with chemo-therapeutic, radiotherapeutic, or immunotherapeutic intervention, in addition to other pro-apoptotic or cell cycle regulating agents.

Alternatively, the present inventive therapy may precede or follow the other agent treatment by intervals ranging from minutes to weeks. In embodiments where the other agent and present invention are applied separately to the individual, one would generally ensure that a significant period of time did not expire between the time of each delivery, such that the agent and inventive therapy would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, present invention is "A" and the secondary agent, such as radio- or chemotherapy, is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

It is expected that the treatment cycles would be repeated as necessary. It also is contemplated that various standard therapies, as well as surgical intervention, may be applied in combination with the inventive cell therapy.

A. Chemotherapy

Cancer therapies also include a variety of combination therapies with both chemical and radiation based treatments. Combination chemotherapies include, for example, abraxane, altretamine, docetaxel, herceptin, methotrexate, novantrone, zoladex, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

In specific embodiments, chemotherapy for melanoma is employed in conjunction with the invention, for example before, during and/or after administration of the invention. Exemplary chemotherapeutic agents for melanoma include at least dacarbazine (also termed DTIC), temozolimide, paclitaxel, cisplatin, carmustine, fotemustine, vindesine, vincristine, or bleomycin.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

Immunotherapeutics generally rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy could thus be used as part of a combined therapy, in conjunction with the present cell therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

Immunotherapy for melanoma may include interleukin-2 (IL-2) or interferon (IFN), for example.

D. Genes

In yet another embodiment, the secondary treatment is a gene therapy in which a therapeutic polynucleotide is administered before, after, or at the same time as the present invention clinical embodiments. A variety of expression products are encompassed within the invention, including inducers of cellular proliferation, inhibitors of cellular proliferation, or regulators of programmed cell death.

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

F. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abililties of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyerproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

EXAMPLES

The following examples are presented in order to more fully illustrate the preferred embodiments of the invention. They should in no way, however, be construed as limiting the broad scope of the invention.

Example 1

Exemplary Materials and Methods

Establishment of cell lines. After informed consent, tumor biopsies (from metastatic skin lesions) were obtained from five patients with stage III or IV melanoma. The tumor tissue was minced and the fragments resuspended in 30 mL of digestion medium containing DNAse at 30 U/mL, hyaluronidase at 0.1 mg/mL, and collagenase at 1 mg/mL (all from Sigma-Aldrich), in complete medium prepared as follows: DMEM (Cambrex) supplemented with 10% of heat inactivated FCS (HyClone), 200 IU/mL penicillin, 200 mg/mL streptomycin, 100 mg/mL gentamicin (Invitrogen), and 2 mmol/L GlutaMAX (Invitrogen). After 4 h incubation at 37° C. in 5% $CO_2$, the cell suspension supernatant (free of tissue debris) was collected, transferred to a new tube, and then centrifuged at 400×g for 5 min. Cells were resuspended in a 6-well plate in fresh complete medium containing 1 mmol/L sodium pyruvate (Invitrogen), and cultured at 37° C. in 5% $CO_2$. Culture medium was renewed every 72 h. At day 6, the antibiotics present in the complete medium were reduced to 100 IU/mL penicillin and 100 mg/mL streptomycin.

When tumor cells reached confluence, they were transferred to a T25 flask for further amplification. The established tumor cell lines (CLB, SENMA, Plaode, RR-371953, and P1143) were characterized by fluorescence activated cell sorting (FACS) analysis (MCSP and GD2) and immunofluorescence (gp100, MAGE-1, and MART-1). Low passage number (<20) of the primary melanoma cell lines was used in in vitro and in vivo experiments.

Normal mesenchymal stem cells and normal skin fibroblasts were generated in laboratory as previously described (Yvon et al., 2003; Gottschalk et al., 2003), and the K562 cell line was obtained from the American Type Culture Collection. All cell lines were maintained in RPMI (Hyclone) supplemented with 10% heat inactivated FCS, 100

IU/mL penicillin, 100 mg/mL streptomycin, 1 mmol/L sodium pyruvate (Invitrogen), and 2 mmol/L GlutaMAX. Six established melanoma cell lines, isolated from surgical specimens at Istituto Nazionale Tumori, Milan, were also used to screen GD2 expression.

Mononuclear cells. Peripheral blood, obtained after informed consent from normal donors, was processed over Ficoll gradients, and the resulting peripheral blood mononuclear cells (PBMC) were cultured in complete T-cell medium containing 45% RPMI and 45% Click's medium supplemented with 10% heat inactivated FCS, 100 IU/mL penicillin, 100 mg/mL streptomycin, and 2 mmol/L GlutaMAX.

Retroviral constructs. The 14g2a scFv sequence was cloned in the SFG retroviral backbone in frame with the human IgG1-CH2CH3 domain, followed by the CD28 and OX40 endodomains and the ζ-chain of the T-cell receptor/CD3 complex, to form the 14g2a-CD28-OX40-ζ (CAR-GD2) construct as previously described (Pule et al., 2005). Vectors encoding the Firefly Luciferase gene (FF-Luc.) or the eGFP protein were also used to track cell survival and proliferation in vivo, as previously described (Savoldo et al., 2000). The RD114 retrovirus envelope (RDF plasmid) and the MoMLV gag-pol (PegPam3-e plasmid) were used to engineer the retroviral vectors.

Retrovirus production and transduction. Transient retroviral supernatants were produced by cotransfection of 293T cells with the PegPam-e, RDF, and the desired SFG vectors (CAR-GD2, eGFP, or FF-Luc) using the Fugene6 transfection reagent (Roche), and used to transduce OKT3 (Ortho Biotech) activated PBMCs, as previously described (Vera et al., 2006).

The 4405M, CLB, SENMA, and P1143 melanoma cell lines were transfected with retroviral vectors encoding either eGFP or FF-Luc. The inventors plated $1 \times 10^5$ tumor cells in 1 well of a 6-well plate and the cells were grown to 60% to 70% confluency. Culture medium was replaced by the appropriate retroviral supernatant (1.5 mL/well), and 1 μg of polybrene was added. When the tumor cells reached confluency, they were trypsinized and plated in a T25 flask. The FF-Luc-transduced cells were then selected with puromycin (Sigma-Aldrich) at 1 μg/mL. The eGFPtransduced tumor cell lines did not require selection as >98% of the cells were eGFP-positive postretroviral transduction.

Flow cytometry. FITC-, phycoerythrin (PE)-, or periodin chlorophyll protein (perCP)-conjugated anti-CD4, -CD8, -CD80 and -CD86 monoclonal antibodies (all from Becton-Dickinson) were used to label lymphocytes, whereas anti-MCSP-PE (Miltenyi-Biotech Inc.) and a purified anti-GD2 monoclonal antibody (Becton-Dickinson Pharmingen) were used to stain the melanoma cells. A secondary antibody (RAM-IgG2a+b-PE; Becton-Dickinson) was added to detect the anti-GD2 (IgG2a) antibody by indirect immunofluorescence. CAR expression by transduced T lymphocytes was detected using a monoclonal anti-idiotype, 1A7 (TriGem, Titan), followed by staining with the secondary antibody RAM-IgG1-PE (Becton-Dickinson; Rossig et al., 2001). The proliferation of nontransduced and transduced T cells, in the presence or absence of tumor cells, was evaluated by FACS analysis after labeling T cells with CFSE (Invitrogen) according to the manufacturer's instructions.

Cytotoxicity assays. The cytotoxic activity of the nontransduced and CAR-GD2 T lymphocytes was evaluated in a standard $^{51}$Cr release assay, as previously described (Pule et al., 2005; Vera et al., 2006). Isotope release was evaluated at 6 and 18 h in cultures with effector-to-target (E:T) ratios of 40:1, 20:1, 10:1, and 5:1, using a gamma counter (Perkin-Elmer).

Coculture experiments. Seven days after transduction, nontransduced and CAR-GD2 cells were collected, counted, and plated at $5 \times 10^5$ cells/well in a 24-well plate at 20:1 ratio with eGFP-expressing (>98%+) tumor cells. Cytokine release after 24 h of culture was measured using the CBAarray (BD Bioscience) and the percent of CD3-positive T cells and eGFP-positive tumor cells was evaluated by FACS analysis at day 5 of coculture, after treatment with 0.5% trypsin EDTA (Invitrogen) to detach adherent cells.

Xenogeneic SCIDmo use model of melanoma. To assess the in vivo antitumor activity of the CAR-GD2 T lymphocytes, an exemplary SCID mouse model was used and the P1143 or 4405 M melanoma line expressing FF-Luciferase. SCID mice (8 to 9 weeks old) were sublethally irradiated (250 rad) and injected i.v. with $2 \times 10^6$ tumor cells. Tumor cell engraftment was monitored using the IVIS 100 imaging system (Caliper Lifesciences), and on days 4 and 21, $1 \times 10^7$ nontransduced or CAR-GD2 T lymphocytes were injected i.v. The animals were imaged weekly to evaluate tumor growth, and photon emission from luciferase-expressing cells was quantified using the "Living Image" software provided with the IVIS system (Caliper Lifesciences). Briefly, after drawing a region of interest over the tumor region, the intensity of the signal measured was expressed as total photons/s/cm2 (p/s/cm$^2$/sr).

Statistical analysis. For cytotoxicity and cytokine production, results were presented as mean±SD and paired Student's t test was used to determine statistical significance. For the bioluminescence results, the signal intensity was log-transformed and summarized using mean±SD at baseline and multiple subsequent time points for each group of mice. Changes in intensity of signal from baseline at each time point were calculated and compared using paired t-tests or Wilcoxon signed-ranks test. $P<0.05$ was considered statistically significant.

Example 2

Expression of GD2 by Primary Melanoma Cells

To characterize GD2 as a target for CAR-directed T cell therapy, primary melanoma cells were dissociated from five patients after biopsy of cutaneous metastatic melanoma and an additional six established cell lines were used in a study. Cells from the five patients and four of the established lines expressed GD2 on immunofluorescence staining, and between 17% and 95% of the cells were positive, with variable intensity of expression (FIG. 1). Expression of GD2 was used on a normal skin fibroblast cell line and it was confirmed that it did not express the ganglioside. To confirm the absence of normeoplastic cells in the primary culture, expression of MCSP on the cells (Table 1) was examined, and to compare the frequency of expression of GD2 with that of other known melanoma tumor associated antigens, the expression of gp100, MART1, and MAGE-1 was also measured. The percentage range of GD2-positive cells was comparable with the range of malignant cells expressing these three other melanoma-associated antigen cells (Table 1). All cell populations studied were negative for expression of the costimulatory molecules CD80 or CD86.

TABLE 1

Characterization of the melanoma cell lines. Expression of GD2, MCSP, gp100, MART1 and Mage-1 is presented. MCSP and GD2 expression was evaluated by FACS analysis and fluorescence used to determine the expression of gp100, MART1 and Mage-1.

|  | GD2 (%/MFI) | MCSP (%) | gp100 (%) | MART1 (%) | Mage-1 (%) |
| --- | --- | --- | --- | --- | --- |
| CLB | 19/182 | 100 | 99 | 11 | 46 |
| SENMA | 45/884 | 100 | 92 | 80 | 98 |
| PLAODE | 22/219 | 100 | 11 | 22 | 3 |
| RR-371952 | 17/775 | 100 | 47 | 99 | 1 |
| P1143 | 95/838 | 10 | 100 | 92 | 10 |
| 18588M | 85/162 | 100 | 1 | 3 | 80 |
| 18732M | 93/150 | 100 | 99 | 76 | 26 |
| 4405M | 0/NA | 100 | 26 | 9 | 1 |
| 10538P | 80/142 | 100 | 57 | 14 | 62 |
| 879M | 0/NA | 100 | 59 | 71 | 55 |
| 8959M | 77/71 | 100 | 99 | 32 | 82 |

Figure 2:
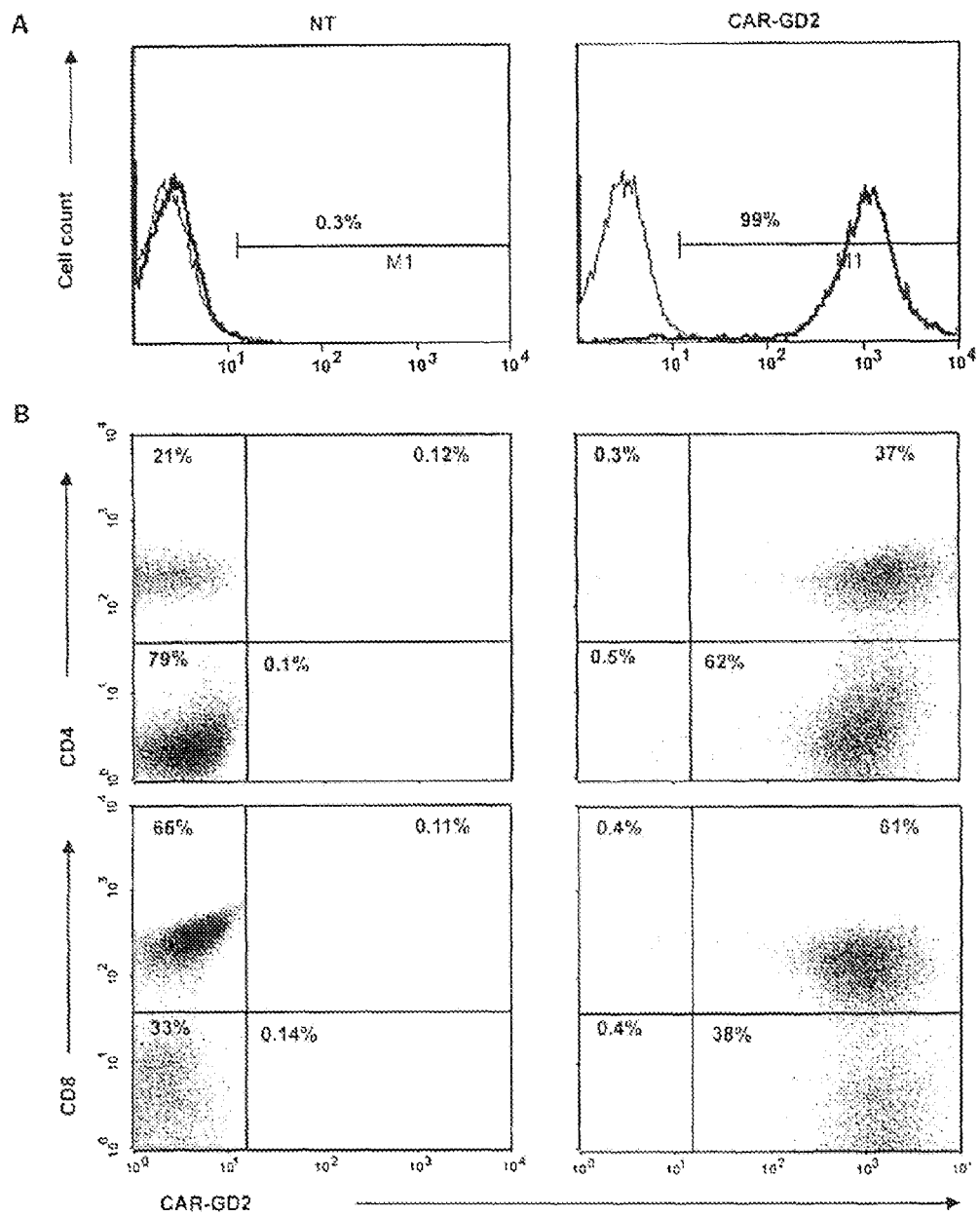
FIGS. 2A-2B demonstrate that T lymphocytes can be genetically modified to express CARs targeting GD2. Activated T lymphocytes were genetically modified to express CAR-GD2.

T cells expressing a GD2-specific chimeric receptor kill GD2-positive melanoma cell lines. T cells from four healthy donors were transduced with a vector encoding the 14g2a single-chain antibody linked to ζ and to the endodomains of the two costimulatory molecules CD28 and OX40, which enhance the activation, proliferation, and cytotoxicity of T cells produced by the CAR after antigen engagement (Pule et al., 2005). Five days after transduction, the expression of GD2-specific CAR was measured by flow cytometry using the anti-14g2a idiotypic antibody 1A7, and it was found that 95% of cells transduced with the 14g2a-CD28-OX40-ζ retroviral vector were CAR positive (range, 93-97%; FIG. 2A). The CAR-GD2 construct transduced CD4-positive and CD8-positive T cell populations with equal efficiency (FIG. 2B).

Figure 3:
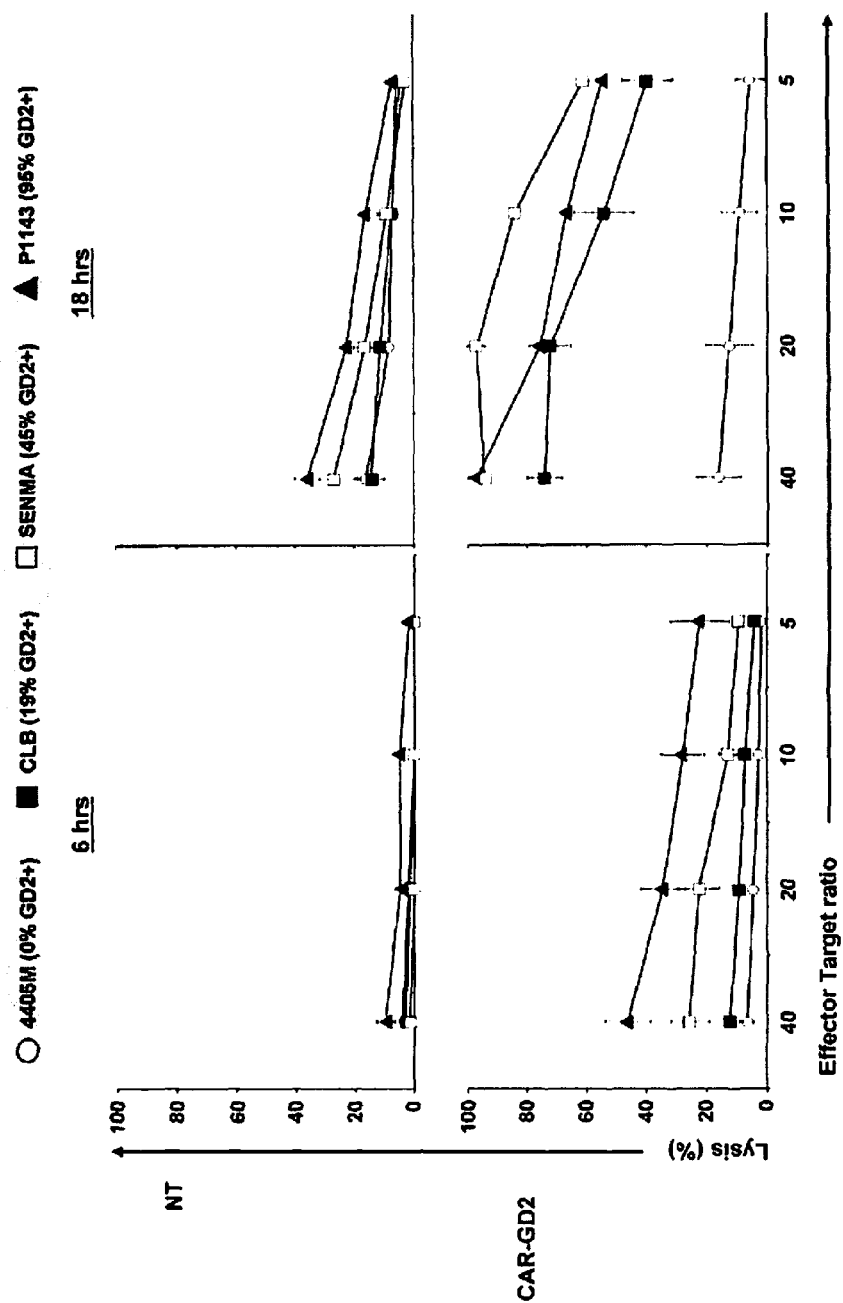
FIG. 3 demonstrates lymphocytes redirected to express CAR-GD2 kill GD2-positive melanoma cell lines. A $^{51}$Cr release assay was used to evaluate the cytotoxic activity of T lymphocytes expressing CAR-GD2 and nontransduced (NT) T cells. Target cells were melanoma lines with absent GD2 (4405 M) or low (CBL), intermediate (SEMMA), or high (P1143) GD2 expression. Left and right graphs, mean and SD of $^{51}$Cr release from four T cell lines after 6 and 18 h incubation, respectively.
Figure 7:
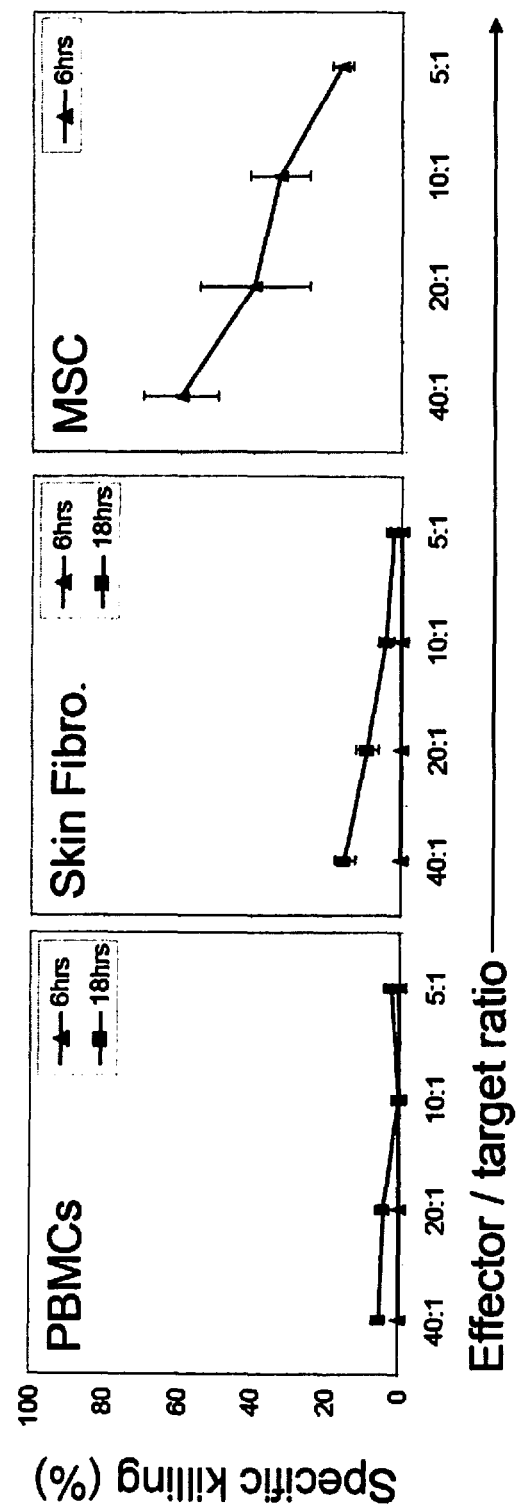
FIG. 7 shows cytolytic activity of T-lymphocytes redirected to express GD2-CAR against normal cell lines. The inventors used a $^{51}$CR release assay to evaluate the cytotoxic activity of T lymphocytes expressing CAR-GD2. Target cells were allogeneic peripheral blood mononuclear cells (PBMCs) and GD2-skin fibroblasts. The inventors also used a GD2+ mesenchymal stem cell (MSC) line, which was susceptible to CAR-GD2 T cell killing. Data illustrate the mean and SD of $^{51}$Cr release from 4 T cell lines after 6 and 18 hours incubation. Non-transduced T cells did not kill any of the targets tested.

To mimic the range of GD2 expression seen on primary melanoma cells, the ability was measured of CAR-GD2 T cells to kill three melanoma cell lines with different GD2 expression. P1143 was a high expressor [95% positive, mean fluorescence intensity (MFI)=838]; SENMA was intermediate (45% positive, MFI=884); CLB was low (19% positive, MFI=182), and finally, the melanoma cell line 4405 M was used as a GD2-negative tumor cell control. At 6 hours and 18 hours, $^{51}$Cr release assays showed that the antitumor activity was proportional to the level of GD2 antigen expression (FIG. 3). As anticipated, the CAR-GD2 T cells had little activity against the GD2-negative tumor cell line (4405 M), the GD2-NK-cell target line K562, or against normal skin fibroblasts or PBMCs that are also GD2 negative (FIG. 7).

CAR-GD2 T cells were, however, able to kill a mesenchymal stem cell line positive for GD2 (95% positive, MFI=799; FIG. 7). Of note, such cross-reactivity with GD2-positive normal mesenchymal stem cells has not produced discernible adverse effects in any clinical trial of GD2 monoclonal antibodies in patients with neuroectodermal tumors (Saleh et al., 1995; Murray et al., 1995) or in a phase I study of CAR-GD2 T cells in patients with neuroblastoma (Pule et al., 2008).

CAR-GD2-expressing T cells secrete cytokines upon stimulation with GD2-expressing melanoma cells. Functional activation of CAR-GD2-expressing T cells following their exposure to GD2-positive melanoma cells was measured by cytokine release assay. As described above, GD2-positive target cells were killed by T cells expressing the CAR, and significant interleukin 2 (IL-2), IL-5, IFN-γ, and tumor necrosis factor α (TNF-α) release occurred during coculture with the three melanoma lines.

Figure 4:
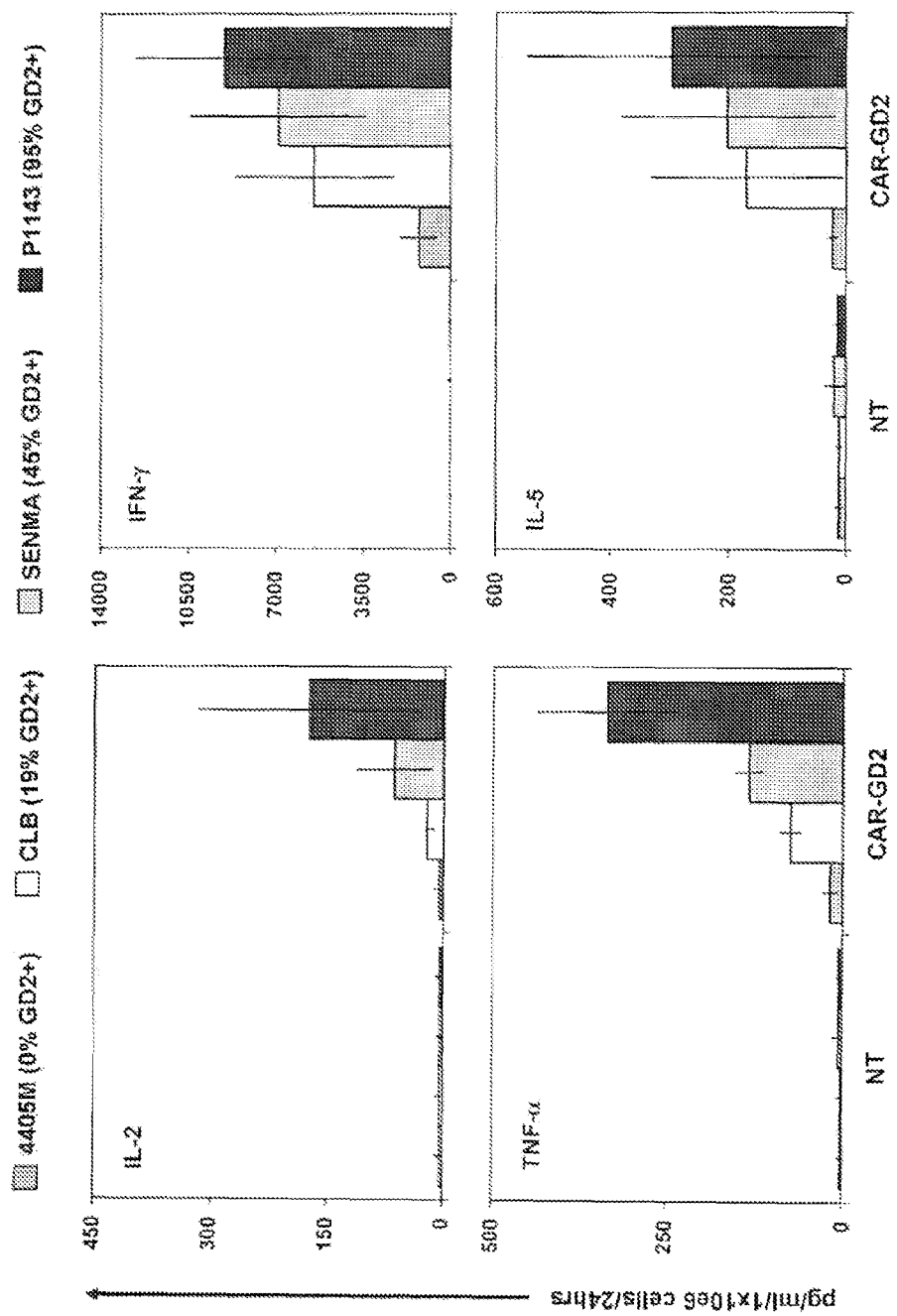
FIG. 4 shows T lymphocytes expressing GD2-CAR produce Th1 and Th2 cytokines in response to GD2-positive melanoma cell lines. T lymphocytes transduced with CAR-GD2 or nontransduced (NT) T cells were cocultured (ratio T lymphocytes:tumor cells of 20:1) with four different melanoma cell lines either negative for GD2 (4405 M) or expressing dim (CBL), intermediate (SEMMA), or high (P1143) levels of GD2. Culture supernatant was collected 24 h later and the production of IL-2, IL-5, IFN-γ, and TNF-α measured using a CBA assay. Neither IL-4 nor IL-10 was detected in the 24-h supernatants. The results of four experiments are presented.

As FIG. 4 shows, the quantity of IL-2, IL-5, IFN-γ, and TNF-α secreted by the CAR-GD2 T cells after 24 hours of culture correlated with the level of GD2 expression on the target cells, and was highest for P1143 and lowest for CLB. Neither IL-4 nor IL-10 was detected in the supernatants of stimulated cells.

CAR-GD2 induces sustained killing and clonal expansion in coculture experiments. It was next determined whether the killing and cytokine release mediated by CAR-GD2 T cells could lead to CAR-T cell proliferation and tumor cell eradication in vitro in a 5-day coculture experiment. CFSE-labeled control or CAR-GD2 T cells were used to determine whether CAR stimulation by CAR-GD2-expressing T cells induces effector T cell proliferation.

Figure 5:
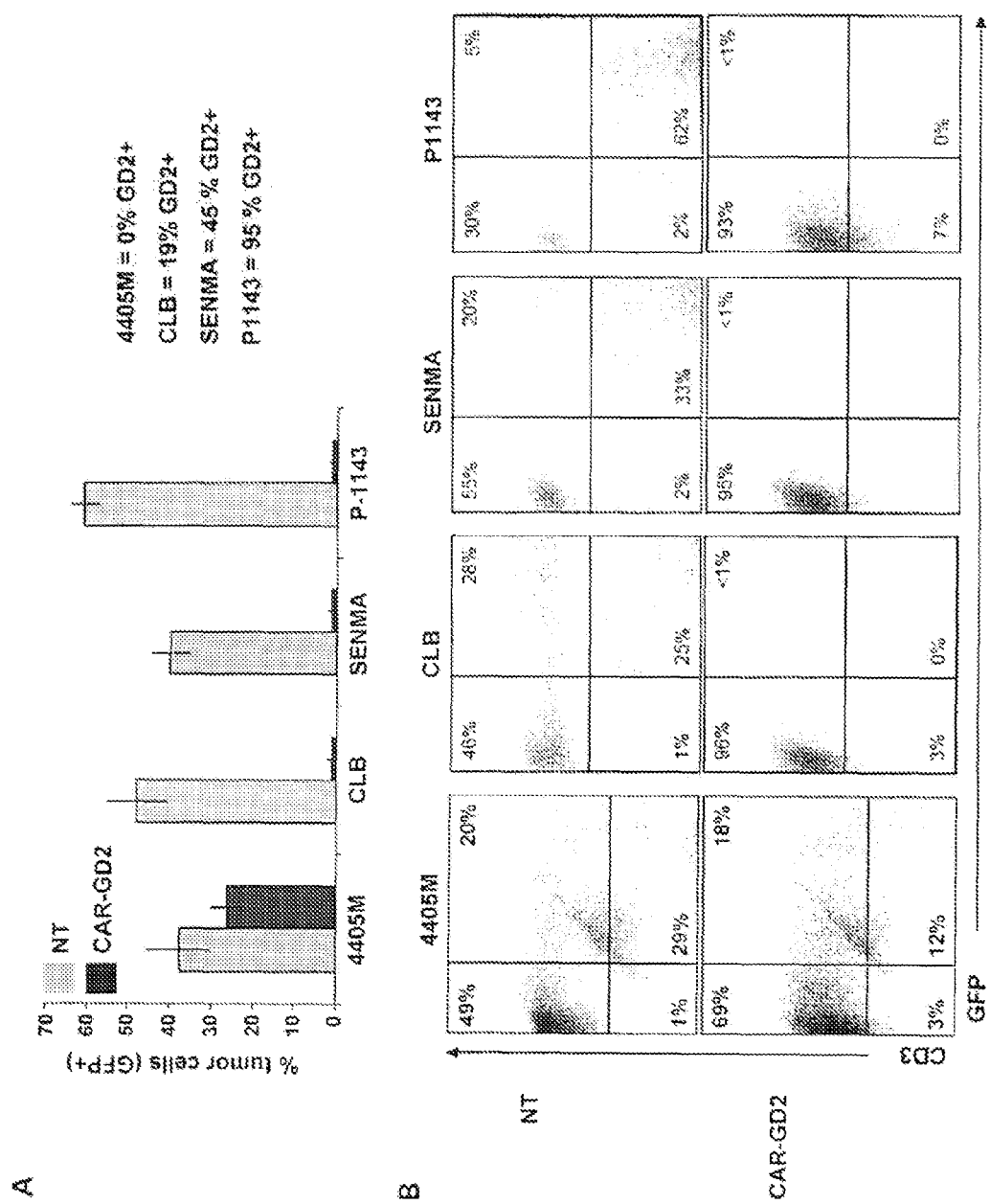
FIGS. 5A and 5B provide T-lymphocytes redirected to express CAR-GD2 eliminate GD2-positive melanoma cell lines in vitro. To evaluate the capacity of T lymphocytes expressing CAR-GD2 to eliminate melanoma cells, nontransduced (NT) or CAR-GD2 transduced T lymphocytes were cultured with melanoma cell lines that were GD2-negative (4405 M) or expressed dim (CBL), intermediate (SEMMA), or high (P1143) levels of the target antigen. T lymphocytes and melanoma cell lines were plated at 20:1 ratio and cultured for 5 d without adding IL-2 to the culture. Residual melanoma cells were enumerated by FACS analysis.
Figure 8:
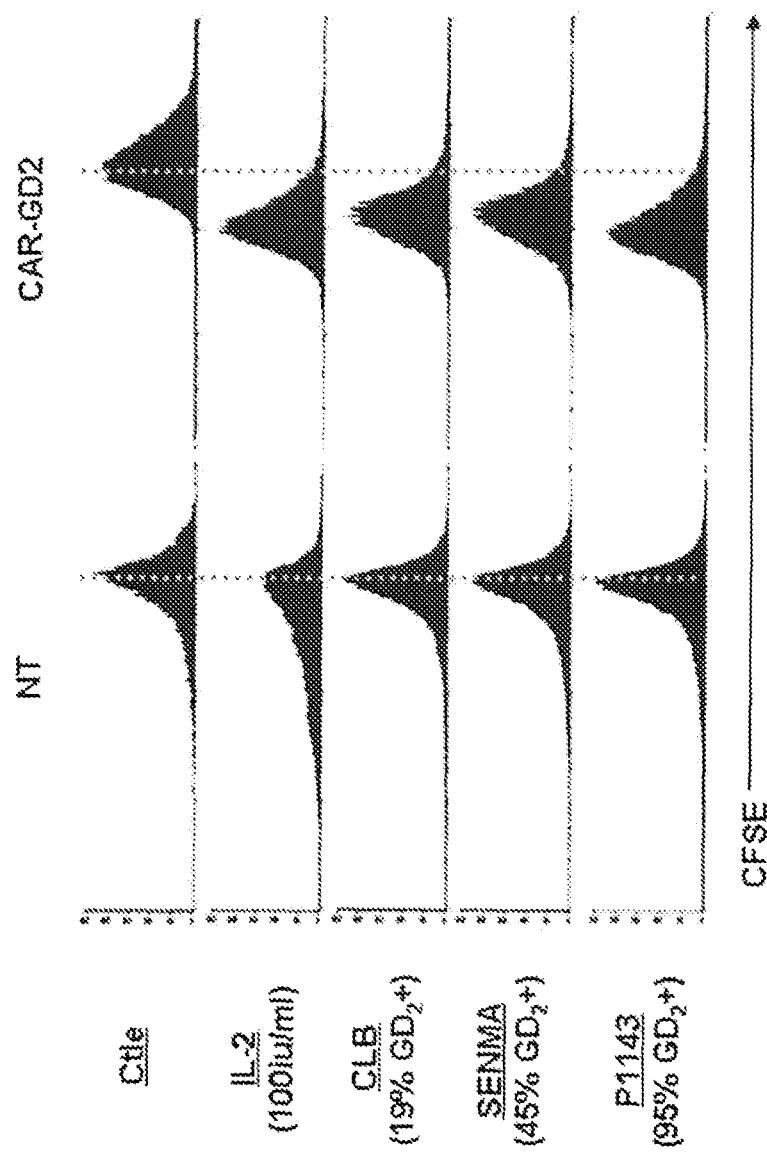
FIG. 8 shows T lymphocytes expressing CAR-GD2 and co-expressing CD28-OX40 endodomains proliferate in response to GD2+ melanoma cell lines. CAR-GD2 T cells labeled with CFSE, to evaluate T cell division, were co-cultured (Ratio T cells: tumor cells of 20:1) with three melanoma cell lines expressing dim (CLB), intermediate (SENMA) or high (P1143) levels of GD2. Non transduced (NT) T lymphocytes were used as negative controls. CFSE expression by T cells was analyzed by FACS on day 4. Only T cells expressing CAR-GD2 divided multiply in response to GD2+ melanoma cell lines. Data are representative of repeat experiments.

Nontransduced T cells proliferated only in the presence of exogenous IL-2 (100 U/mL), whereas proliferation of CAR-expressing T cells increased in response to all three GD2-expressing tumor cell lines, irrespective of whether these tumor cells expressed high, intermediate, or low levels of GD2 (FIG. 8). To discover if these expanded CAR-GD2 T cells were functional, tumor cells were labeled with eGFP and were cocultured at the CAR-T cell:tumor cell ratio of 20:1 in the absence of IL-2. After 5 days of culture, viable GFP-positive cells were enumerated by flow cytometric analysis. FIG. 5 shows that viable tumor cells were eradicated in cocultures with T cells expressing CARGD2 but not in cocultures with nontransduced T cells. Hence CAR-GD2 T cells proliferate in vitro in response to the GD2 antigen and eradicate melanoma cells that express the antigen. As expected, the GD2-negative cell line 4405 M was not killed in the 5-day coculture experiment, showing GD2 antigen recognition is essential for the activity of CAR-GD2-expressing T cells.

Adoptive transfer of GD2-specific T cells provide antitumor effect in a xenogeneic SCIDmodel. The antitumor activity was measured of CAR-GD2 T cells in vivo. To monitor tumor cells in vivo, the firefly luciferase (FFLuc) gene was expressed in 4405 M and P1143 cells, together with the puromycinresistance gene. After puromycin selection, $2\times10^6$ FFLuc-P1143 or 4405 M tumor cells were injected i.v. into SCID mice.

Figure 6:
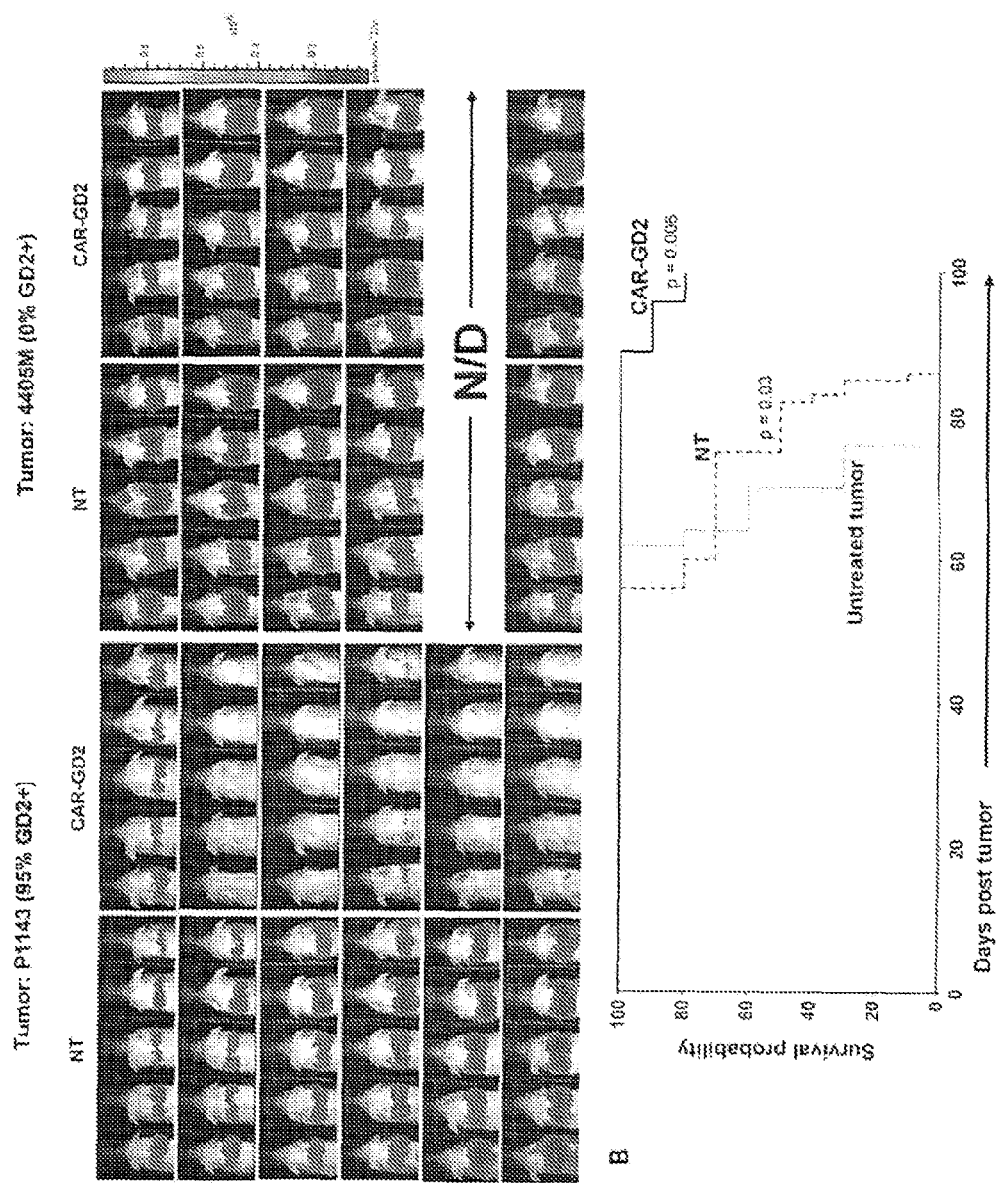
FIG. 6 demonstrates that CAR-GD2 T lymphocytes control tumor growth in vivo. SCID mice were infused i.v. with 2×10$^6$ melanoma cells from the cell lines 4405 M (0% GD2 positive) or P1143 (95% GD2 positive) labeled with FFLuc gene. Tumor growth and engraftment was monitored using an in vivo imaging system (Xenogen-IVIS Imaging System). Four and 21 d after tumor infusion, mice were treated with T lymphocytes CAR-GD2 or nontransduced (NT) T cells (1×10$^7$ cells/mouse). No exogenous cytokines were injected into the mice. A, tumor growth measured as light emission in a representative cohort of 5 mice from each group of NT and CAR-GD2 T cell-treated animals. B, survival curve of mice engrafted with the P1143 (95% GD2 positive) tumor cells receiving either tumor alone, NT T cells or CAR-GD2 T lymphocytes.

After 4 days, FFLuc expression was evaluated by bioluminescence imaging and the mice were divided into three groups that received nontransduced T cells or T cells expressing CAR-GD2 at $1\times10^7$ i.v. and finally a group that received tumor cells alone. A second injection of nontransduced or CAR-GD2 T cells was given at day 21 and luciferase signal was measured every week in the 10 mice of each of the groups. FIG. 6A shows five representative mice from the nontransduced and CAR-GD2 T cells group, and shows that tumor grew rapidly in the lungs of mice receiving nontransduced T cells. By contrast, the tumors in mice receiving T cells expressing CAR-GD2 diminished within 48 to 72 hours of injection, and luciferase derived remained largely absent in the group receiving CARGD2 T cells. Although the survival of the mice receiving the tumor cells alone or tumor cells plus nontransduced T cells was 68±6 days and 72±12 days, respectively (P=0.03), 80% of the mice from the group receiving CAR-GD2 T cells were still alive at day 100 and showed a significant survival advantage when receiving CAR-GD2-specific T cells (P=0.006; FIG. 6B). Finally, no tumor regression was reserved when CAR-GD2 T cells were infused in mice bearing GD2-4405 M tumor cells (FIG. 6A).

Example 3

Significance of Certain Embodiments of the Invention

In particular aspects of the invention, the ganglioside antigen GD2 is expressed on the majority of primary melanoma cell lines, and T cells engineered to express a CAR directed to this antigen are able to recognize and lyse GD2-positive melanoma target cells in vitro and in a SCID mouse model in vivo. The transgenic receptor construct included the signaling endodomains of the CD28 and OX40 costimulatory molecules, and redirected T cells showed activation, proliferation, and cytokine release after T-cell receptor engagement by GD2.

Melanoma has long been a target of cellular immunotherapies directed to the tumor-associated antigens expressed by the malignant cells. Although earlier clinical research focused on reinfusion of expanded tumor infiltrating lymphocytes, efforts have recently been directed against the cancer testis series of antigens such as MAGE and the melanocyte differentiation proteins such as MART-1, by generation of T cells expressing conventional αβ-T-cell receptors specific for these antigens. These receptors recognize peptide fragments in association with MHC class I molecules, and are therefore restricted in their patient range to individuals with the appropriate MHC polymorphism. Moreover, they are unable to recognize tumor subclones in which the antigen processing machinery is deficient. T cells that express synthetic or chimeric receptors that recognize unprocessed structures on the cell surface may thus have an advantage over T cells whose tumor reactivity is mediated through their native receptor.

It has been known for some time that the ganglioside GD2 is expressed by tumors derived from neuroectoderm, including neuroblastoma, sarcoma, and small lung cancer. This tumor-associated carbohydrate antigen is also expressed by many melanoma cells (Cheresh et al., 1984), in which it is involved in cell adhesion and may contribute to metastasis (Hakomori, 2001). Although GD2 is present on the surface of many melanoma cells, it is absent on most normal tissue, with only limited expression in brain and on peripheral nerves, making this ganglioside an attractive target for adoptive cell therapy in metastatic melanoma (Hersey et al., 1998).

GD2 monoclonal antibodies have already been used with benefit in patients with other GD2-positive malignancies, such as neuroblastoma, but melanoma cells have more variable (and usually lower) expression of the antigen. Hence, the benefits of GD2 antibody infusion in melanoma have been limited (Saleh et al., 1992; Murray et al., 1994). The level of GD2 expression on melanoma cells, however, is evidently sufficient to produce a cytotoxic response from T cells expressing the same monoclonal antibody binding site in the form of a chimeric T-cell receptor. There was complete killing of the tumor cells even when GD2 expression was low, consistent with previous observations that even tumor cells with dim expression of the targeted antigen can be eliminated by CAR-modified T cells (Vera et al., 2006). The killing of cells that are resistant to antibodies of the same specificity may be related to the improved avidity of multiple antibody-derived binding domains when they are arrayed on a cell surface rather than existing as bivalent molecules in solution, or it may reflect a superior cytolytic activity of T effector cells compared with antibody (Weijtens et al., 2007).

Hence, tumor cells with dim antigen expression can be completely eliminated after coculture experiments, even when short term assays based on $^{51}$Cr release assay may produce lower immediate cytotoxicity than tumor cells with high antigen expression Like most malignancies, melanoma cells lack expression of the T-cell costimulatory molecules required for complete activation of T lymphocytes that engage tumor-associated antigens through their native or chimeric receptors. Hence, to optimize T cell triggering and effector function, the chimeric receptor was coupled to co-stimulatory endodomains to increase T cell survival and expansion. Following CAR engagement, endodomains from single co-stimulatory molecules, such as CD28, 4-1BB, or OX40, into the CAR may be sufficient to activate the cellular components of the killing machinery and to produce IL-2 release and T cell proliferation (Willemsen et al., 2005; Imai et al., 2004). It has been previously shown, however, that the simultaneous expression in cis of two endodomains such as CD28 and OX40 within a GD2-CAR produces superior T cell proliferation and effector function than expression of a single costimulatory endodomain (Pule et al., 2005). In certain embodiments, this benefit occurs because both CD28 and OX40 signals are both functional, and produce greater activation of NF-κB than either endodomain alone, because they act through two independent pathways (Pule et al., 2005).

If adoptive transfer of CAR-modified T cells in melanoma is to be of clinical value, it will be essential to be able to treat metastatic disease. Accordingly, the effects of the CAR-GD2 T cells were studied in an exemplary xenograft lung metastatic model. Human T cells expressing the 14g2a-CD28-OX40-ζ CAR produced significant antitumor activity in this model, but were unable to completely eradicate the disease. This incomplete benefit may reflect the difficulties of sustaining human T cell function and trafficking in a xenogeneic environment, or it may also represent the limitations of even the combination of CD28 and OX40 endodomains, which on their own cannot completely recapitulate the temporo-spatial features of the costimulatory events required to sustain T cell activation physiologically (Pule et al., 2008; Heemskerk et al., 2004).

Thus, in aspects of the invention, GD2 on melanoma cells is a useful target for CAR-T cells. Administration of such cells will usefully complement other cellular immunotherapies and biotherapies for this disease, in at least some embodiments.

Example 4

Figure 9A:
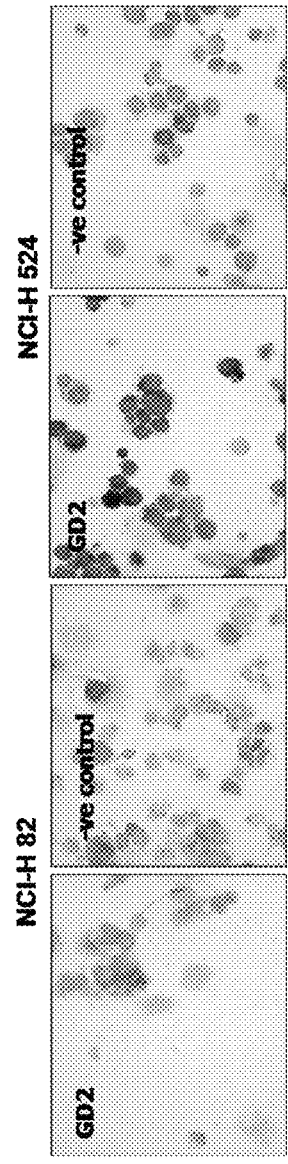
FIGS. 9A-9B show GD2 expression in lung cancer.
Figure 9B:
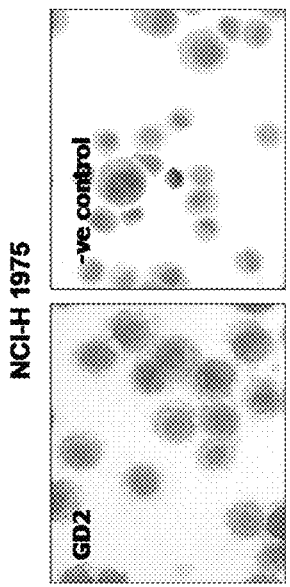

Targeting the Disialo-Ganglioside Gd2 in Lung Cancer Using Chimeric Antigen Receptor(CAR) T Lymphocytes FIGS. 9A-9B demonstrate GD2 expression in lung cancer: To study the expression of GD in lung cancer cell the inventors performed cytochemistry on a number of lung cancer cytospin specimens and flow cytometry. FIG. 9A shows expression in small cell lung cancer, and FIG. 9B shows expression in non-small cell lung cancer.

Figure 10:
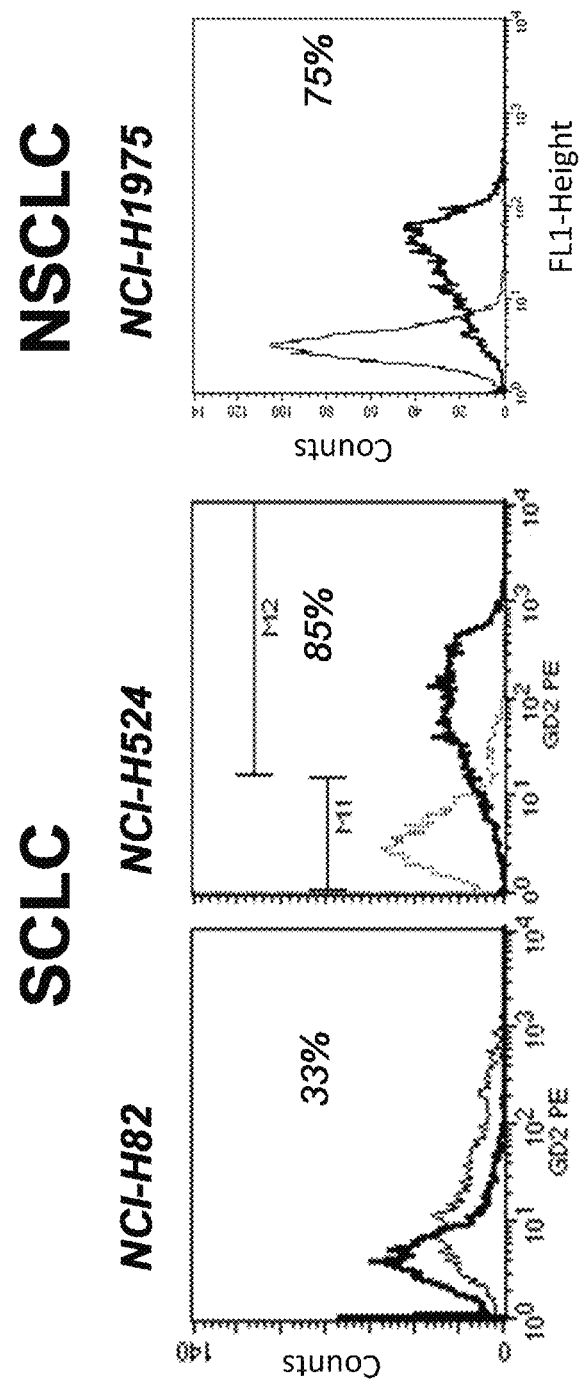
FIG. 10 shows flow cytometry for both small cell and non small cell lung cancer.

These findings were validated using flow cytometry for both small cell lung cancer and non-small cell lung cancer (FIG. 10).

Figure 11:
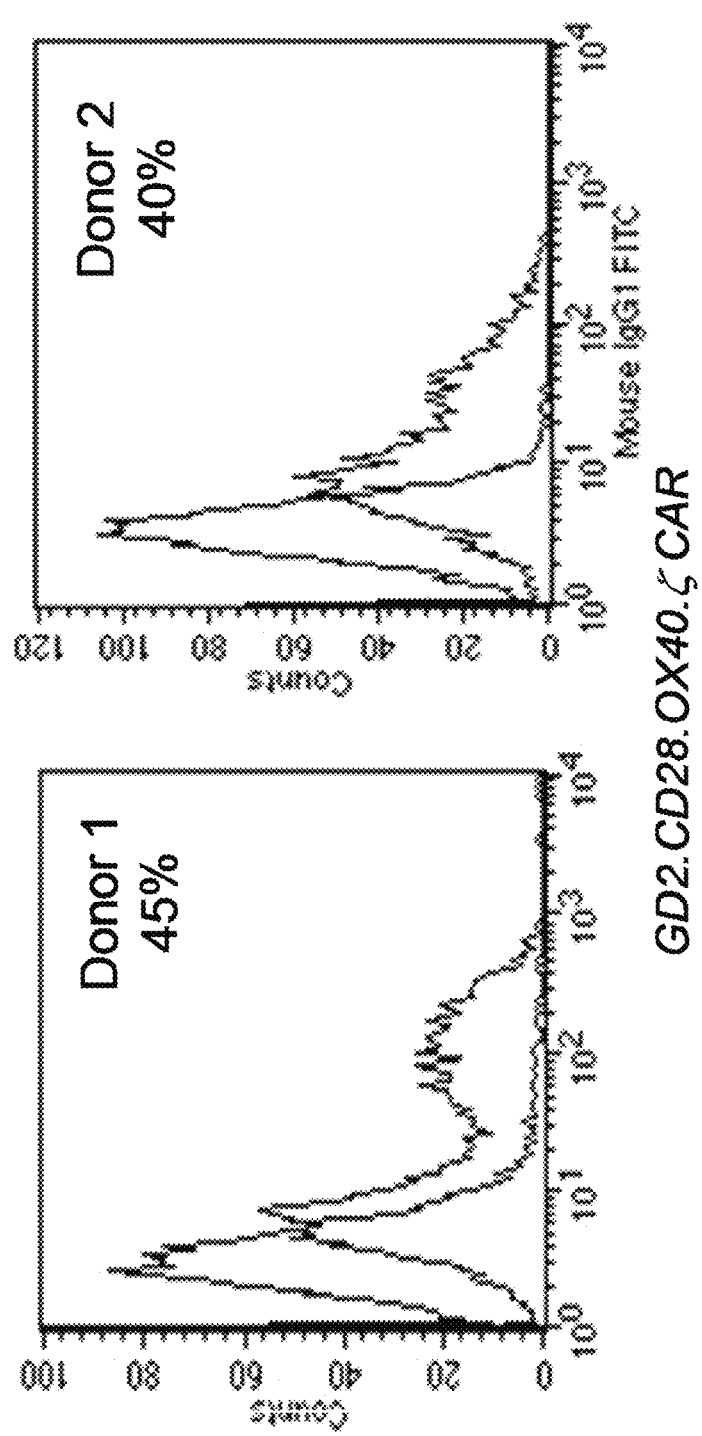
FIG. 11 shows transduction rates with GD2 CAR using GD2 specific proteins.

Transduction of T lymphocytes was employed to express GD2 CD28.zeta CAR. The inventors used a retroviral system to transduce human peripheral blood lymphocytes to express the GD2-specific third generation CAR molecule with a CD28, OX40 and zeta signaling domains (FIG. 11). More than 50% transduction rates was consistently obtained with various donors.

Figure 12A:
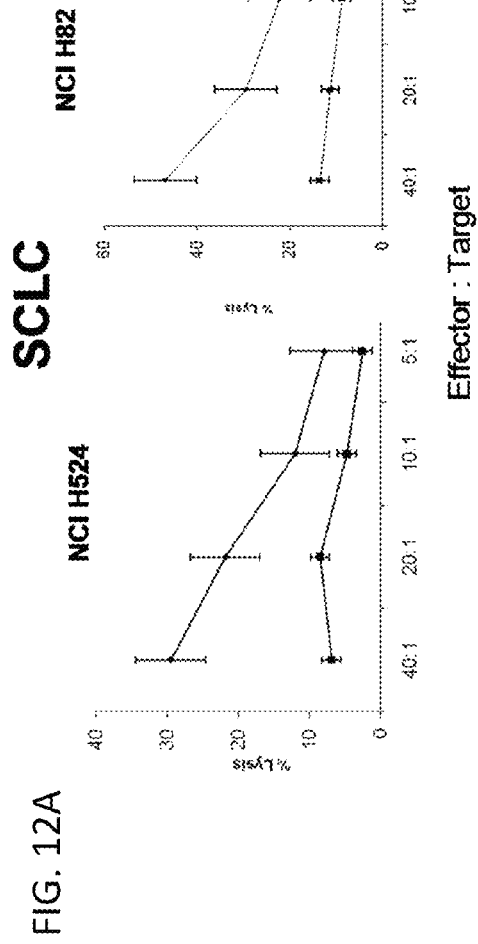
FIGS. 12A-12B demonstrate that GD2 CAR-transduced T lymphocytes recognize and kill lung cancer cell lines.
Figure 12B:
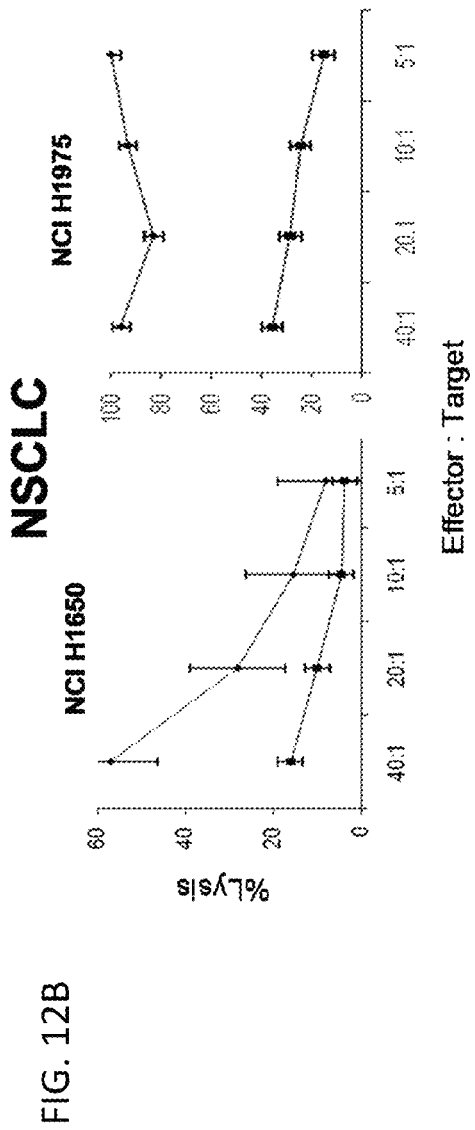

In FIGS. 12A-12B, GD2 CAR-transduced T lymphocytes recognize and kill lung cancer cell lines. The inventors used standard 4-6 hour $^{51}$Cr release assays to assess the degree of cytolysis of exemplary lung cancer cell lines at various tumor to T cell ratios. The neuroblastoma cell line LAN1 was used as a positive control. Lymphoblastoid cell lines (LCL) were used as the negative control. FIG. 12A shows killing of small cell lung cancer, and FIG. 12B shows killing of non-small cell lung cancer.

Figure 13:
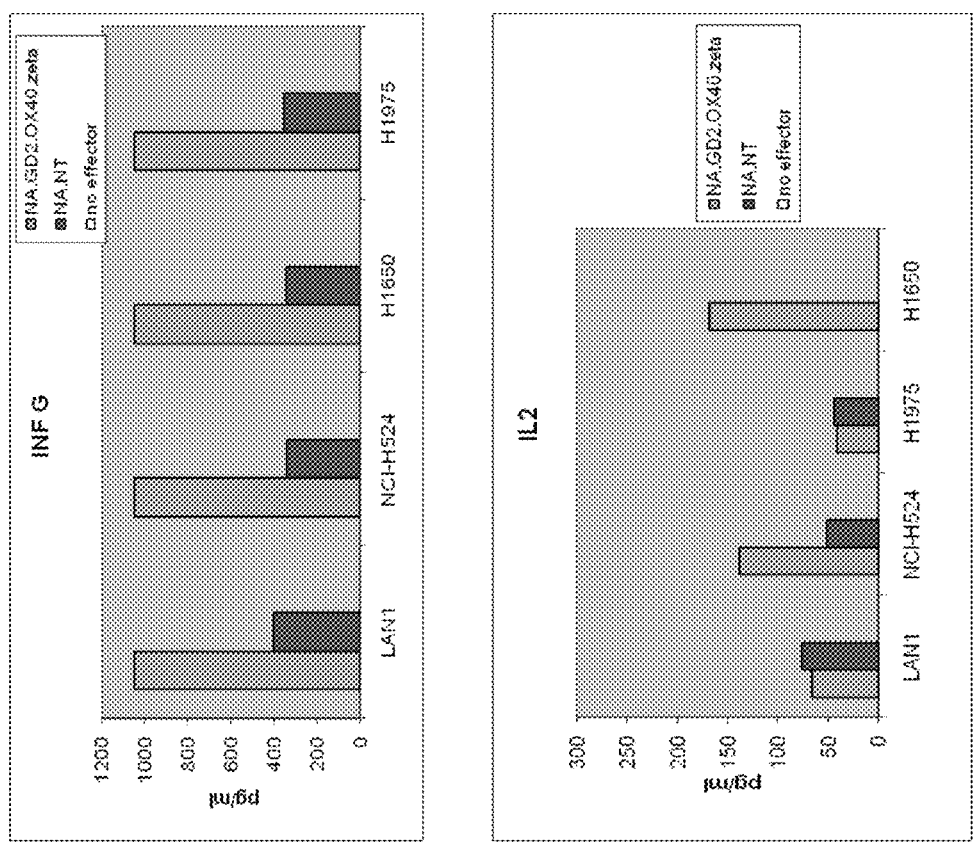
FIG. 13 demonstrates that GD2 CAR-transduced T lymphocytes secrete immunostimulatory cytokines in coculture of GD2 positive lung cancer cell lines.

GD2 CAR-transduced T lymphocytes secrete immunostimulatory cytokines in coculture of GD2 positive lung cancer cell lines (FIG. 13). ELISA was performed to detect the cytokine release (IFNγ and IL-2) 24 to 48 hours after co-culture initiation. GD2 expressing T cells secreted immunostimulatory cytokines upon encounter of GD2 positive lung cancer cells above non-transduced controls from the same donor.

REFERENCES

All patents and publications mentioned in this specification are indicative of the level of those skilled in the art to which the invention pertains. All patents and publications herein are incorporated by reference to the same extent as if each individual publication was specifically and individually indicated to be incorporated by reference in their entirety.

Albino A P, Sozzi G, Nanus D M, Jhanwar S C, Houghton A N. Malignant transformation of human melanocytes: induction of a complete melanoma phenotype and genotype. Oncogene 1992; 7:2315-21.

Bajetta E, Del Vecchio M, Bernard-Marty C, et al. Metastatic melanoma: chemotherapy. Semin Oncol 2002; 29:427-45.

Butler M O, Lee J S, Ansen S, et al. Long-lived antitumor CD8+ lymphocytes for adoptive therapy generated using an artificial antigen-presenting cell. Clin Cancer Res 2007; 13:1857-67.

Cheresh D A, Harper J R, Schulz G, Reisfeld R A. Localization of the gangliosides GD2 and GD3 in adhesion plaques and on the surface of the human melanoma cells. Proc Natl Acad Sci USA 1984; 81:5767-71.

Gottschalk S, Edwards O L, Sili U, et al. Generating CTLs against subdominant Epstein-Ban virus LMP1 antigen for the adoptive immunotherapy of EBV-associated malignancies. Blood 2003; 101:1905-12.

Hakomori S. Tumor-associated carbohydrate antigens defining tumor malignancy: basis for development of anticancer vaccines. Adv Exp Med Biol 2001; 491:369-402.

Haynes N M, Trapani J A, Teng M W, et al. Single-chain antigen recognition receptors that costimulate potent rejection of established experimental tumors. Blood 2002; 100:3155-63.

Heemskerk M H M, Hoogeboom M, Hagedoorn R, Kester M G D, Willemze R, Falkenburg F J H. Reprogramming of virus-specific T cells into Leukemia-reactive T cells using T cell receptor gene transfert. J Exp Med 2004; 199:885-94.

Hersey P, Jamal O, Henderson C, Zardawi I, D'Alessandro G. Expression of the gangliosides GM3, GD3 and GD2 in tissue sections of normal skin, naevi, primary and metastatic melanoma. Int J Cancer 1988; 41:336-43.

Imai C, Mihara K, Andreansky M, et al. Chimeric receptors with 4-1BB signaling capacity provoke potent cytotoxicity against acute lymphoblastic leukemia. Leukemia 2004; 18:676-84.

Jemal A, Siegel R, Ward E, et al. Cancer statistics, 2008. CA Cancer J Clin 2008; 58:71-96.

Livingston P., Ganglioside vaccines with emphasis on GM2. Semin Oncol 1998; 25:636-45.

Livingston P O, Wong G Y, Adluri S, et al. Improved survival in stage III melanoma patients with GM2 antibodies: a randomized trial of adjuvant vaccination with GM2 ganglioside. J Clin Oncol 1994; 12:1036-44.

Mackensen A, Meidenbauer N, Vogl S, Laumer M, Berger J, Andreesen R. Phase I study of adoptive T-cell therapy using antigen-specific CD8+ T cells for the treatment of patients with metastatic melanoma. J Clin Oncol 2006; 24:5060-9.

Morgan R A, Dudley M E, Wunderlich J R, et al. Cancer regression in patients after transfer of genetically engineered lymphocytes. Science 2006; 314:126-9.

Murray J L, Cunningham J E, Brewer H, et al. Phase I trial of murine monoclonal antibody 14G2a administered by prolonged intravenous infusion in patients with neuroectodermal tumors. J Clin Oncol 1994; 12:184-93.

Ohnmacht G A, Marincola F M. Heterogeneity in expression of human leukocyte antigens and melanoma-associated antigens in advanced melanoma. J Cell Physiol 2000; 182:332-8.

Pule M, Finney H, Lawson A. Artificial T-cell receptors. Cytotherapy 2003; 5:211-26.

Pule M A, Savoldo B, Myers G D, et al. Virus-specific T cells engineered to coexpress tumor-specific receptors: persistence and antitumor activity in neuroblastoma patients. Nat Med 2008; 14:1264-70.

Pule M A, Straathof K C, Dotti G, Heslop H E, Rooney C M, Brenner M K. A chimeric T cell antigen receptor that augments cytokine release and supports clonal expansion of primary human T cells. Mol Ther 2005; 12:933-41.

Ragupathi G, Livingston P O, Hood C, et al. Consistent antibody response against ganglioside GD2 induced in patients with melanoma by a GD2 lactone-keyhole limpet hemocyanin conjugate vaccine plus immunological adjuvant QS-21. Clin Cancer Res 2003; 9:5214-20.

Ravindranath M H, Muthugounder S, Presser N. Ganglioside signatures of primary and nodal metastatic melanoma cell lines from the same patient. Melanoma Res 2008; 18:47-55.

Rosenberg S A, Dudley M E. Cancer regression in patients with metastatic melanoma after the transfer of autologous antitumor lymphocytes. Proc Natl Acad Sci USA 2004; 101:14639-45.

Rosenberg S A, Restifo N P, Yang J C, Morgan R A, Dudley M E. Adoptive cell transfer: a clinical path to effective cancer immunotherapy. Nat Rev Cancer 2008; 8:299-308.

Rossig C, Bollard C M, Nuchtern J G. Targeting of G(D2)-positive tumor cells by human T lymphocytes engineered to express chimeric T-cell receptor genes. Int J Cancer 2001; 94:228-36.

Saleh M N, Khazaeli M B, Wheeler R H, et al. Phase I trial of the murine monoclonal anti-GD2 antibody 14G2a in metastatic melanoma. Cancer Res 1992; 52:4342-7.

Savoldo B, Rooney C M, Di Stasi A, et al. Epstein Barr virus specific cytotoxic T lymphocytes expressing the anti-CD30 artificial chimeric T-cell receptor for immunotherapy of Hodgkin disease. Blood 2007; 110:2620-30.

Tsuchida T, Sazton R E, Morton D L, Irie R F. Gangliosides of human melanoma. Cancer 1989; 63:1166-74.

Vera J, Savoldo B, Vigouroux S, et al. T lymphocytes redirected against the κ light chain of human immunoglobulin efficiently kill mature B lymphocyte-derived malignant cells. Blood 2006; 108:3890-7.

Weijtens M E, Hart E H, Bolhuis R L. Functional balance between T cell chimeric receptor density and tumor associated antigen density: CTL mediated cytolysis and lymphokine production. Gene Ther 2000; 7:35-42.

Willemsen R A, Ronteltap C, Chames P, Debets R, Bolhuis R L H. T cell retargeting with MHC class I-restricted antibodies: the CD28 costimulatory domain enhances antigen-specific cytotoxicity and cytokine production. J Immunol 2005; 174:7853-8.

Yun C O, Nolan K F, Beecham E J, Reisfeld R A, Junghans P. Targeting of T lymphocytes to melanoma cells through chimeric anti-GD3 immunoglobulin T-cell receptors. Neoplasia 2000; 2:449-59.

Yvon E S, Vigouroux S, Rousseau R F, et al. Overexpression of the Notch ligand, Jagged-1, induces alloantigen-specific human regulatory T cells. Blood 2003; 102:3815-21.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of treating melanoma or non small cell lung cancer in an individual, comprising the steps of administering to an individual cytotoxic T lymphocytes having a chimeric receptor that recognizes a GD2 antigen on the surface of cancer cells, wherein the chimeric receptor comprises the cytoplasmic signaling domain of the T-cell receptor zeta chain and comprises the cytoplasmic signaling domain of one or more costimulatory molecules selected from the group consisting of CD28, OX40, 4-1BB, and a combination thereof.

2. The method of claim 1, wherein the chimeric receptor comprises antibody that binds GD2.

3. The method of claim 2, wherein the antibody is a scFv antibody.

4. The method of claim 2, wherein the antibody is the 14g2a scFv antibody.

5. The method of claim 1, wherein the individual has had and/or is having an additional cancer therapy for the respective melanoma or non small cell lung cancer.

* * * * *